(12) United States Patent
Male et al.

(10) Patent No.: US 8,154,194 B2
(45) Date of Patent: Apr. 10, 2012

(54) ORGANIC LIGHT-EMITTING DEVICE

(75) Inventors: Nigel Male, Salisbury (GB); Jonathan Pillow, Cambridge (GB); Martin Humphries, Cambridge (GB)

(73) Assignees: CDT Oxford Limited, Cambridgeshire (GB); Sumitomo Chemical Co. Limited, Tokyo (JP)

( * ) Notice: Subject to any disclaimer, the term of this patent is extended or adjusted under 35 U.S.C. 154(b) by 694 days.

(21) Appl. No.: 12/066,791

(22) PCT Filed: Sep. 15, 2006

(86) PCT No.: PCT/GB2006/003438
§ 371 (c)(1),
(2), (4) Date: Dec. 12, 2008

(87) PCT Pub. No.: WO2007/031773
PCT Pub. Date: Mar. 22, 2007

(65) Prior Publication Data
US 2009/0091247 A1 Apr. 9, 2009

(30) Foreign Application Priority Data
Sep. 16, 2005 (GB) .................................. 0518968.3

(51) Int. Cl.
*H01J 1/63* (2006.01)
*C07F 11/00* (2006.01)
*C07F 13/00* (2006.01)
(52) U.S. Cl. ........................................ 313/504; 548/108
(58) Field of Classification Search .................. 428/690, 428/917, 411.1, 336; 313/502–509; 257/40, 257/88, 104, E51; 548/305.1, 101, 103; 585/27
See application file for complete search history.

(56) References Cited

U.S. PATENT DOCUMENTS

| | | | |
|---|---|---|---|
| 5,621,131 | A | 4/1997 | Kreuder et al. |
| 5,723,873 | A | 3/1998 | Yang |
| 5,798,170 | A | 8/1998 | Zhang et al. |
| 6,045,930 | A | 4/2000 | Thompson et al. |
| 6,268,695 | B1 | 7/2001 | Affinito |
| 7,728,137 | B2 | 6/2010 | Stossel et al. |
| 2003/3059647 | | 3/2003 | Thompson et al. |

(Continued)

FOREIGN PATENT DOCUMENTS
EP 0 707 020 A2 4/1996
(Continued)

OTHER PUBLICATIONS

Trofimenko, S. Inorg. Chem., vol. 8, No. 12, (1969), pp. 2675-2680.*

(Continued)

*Primary Examiner* — Angela Ortiz
*Assistant Examiner* — J. L. Yang
(74) *Attorney, Agent, or Firm* — Marshall, Gerstein & Borun LLP (57) ABSTRACT

An organic light-emitting device comprising: an anode; a cathode; a light-emitting layer located between the anode and the cathode, said light-emitting layer containing a light-emitting metal complex comprising general formula 1: (1) where M represents $Re^{(I)}$, $W^{(0)}$, $Ir^{(III)}$, or $Os^{(II)}$; $L_1$ represents a tridentate ligand; and $L_2$, $L_3$ and $L_4$ represent ligands, characterised in that $L_1$ comprises general formula 2:(2) where $R^1$ represents a bridging group; and $Ar^1$, $Ar^2$ and $Ar^3$ each independently represents a group comprising a heteroaryl ring and * indicates coordination to M.

4 Claims, 2 Drawing Sheets

Note: N-N signifies a third indazolyl ring system oriented into the page

U.S. PATENT DOCUMENTS

| | | | |
|---|---|---|---|
| 2003/0194580 | A1 | 10/2003 | Hamada et al. |
| 2004/4091738 | | 5/2004 | Psai et al. |
| 2005/0170207 | A1 | 8/2005 | Ma et al. |

FOREIGN PATENT DOCUMENTS

| | | | |
|---|---|---|---|
| EP | 0 842 208 | A1 | 5/1998 |
| EP | 0 880 303 | A1 | 11/1998 |
| EP | 0 901 176 | A2 | 3/1999 |
| EP | 0 947 123 | A1 | 10/1999 |
| EP | 0 949 850 | A1 | 10/1999 |
| GB | 2 348 316 | A | 9/2000 |
| WO | WO-9806242 | | 2/1998 |
| WO | WO 9806242 | A1 * | 2/1998 |
| WO | WO-98/10621 | A1 | 3/1998 |
| WO | WO-98/57381 | A1 | 12/1998 |
| WO | WO-99/48160 | A1 | 9/1999 |
| WO | WO-00/48258 | A1 | 8/2000 |
| WO | WO-00/53656 | A1 | 9/2000 |
| WO | WO-01/19142 | A1 | 3/2001 |
| WO | WO-01/81649 | A1 | 11/2001 |
| WO | WO-02/084759 | A1 | 10/2002 |
| WO | WO-2004/081017 | A1 | 9/2004 |

OTHER PUBLICATIONS

Trofimenko, S. J. Am. Chem. Soc., 89: 24, pp. 6288-6293.*

Shiu et al. J. Organometallic Chemistry, 372 (1989), pp. 251-261.*

Steyn M. J. Chem. Soc. Dalton Trans. (1990), pp. 2991-2997.*

Collin et al., "Synthesis and Photophysical Propeerties of Iridium(III) Bisterpyridine and Its Homologues: a Family of Complexes with a Long-Lived Excited State," *J. Am. Chem. Soc.*, 121: 5009-5016 (1999).

Sugimoto et al., "Preparation, Spectroscopic Properties, and Dynamic Behavior of a μ-oxo dirhenium(III) complex [$Re_2$(μ-O)$Cl_2$(tpa)$_2$]($PF_6$)$_2$ (tpa=tris(2-pyridylmethyl)amine)," *Inorganica Chimica Acta*, 337:203-211 (2002).

Siegl, "Rhodium(I) and Iridium(I) Carbonyl Compleses with 1,3-BIS(Arylimino)Isoindolines," *Jr. of Organometallic Chem.*, 107:C27-C30 (1976).

International Search Resort for PCT/GB2006/003438 dated Jan. 22, 2007.

Amoroso et al., "Quenching of a Polypyridyl-Ruthenium (II) Chromophore by Covalently Attached {ML(NO)Cl} Fragments (M=Mo, W; L=tris(3,5-dimethylpyrazolyl) hydroborate)," *Inorganica Chimica Acta*, 226(1-2):171-177 (1994).

Bargawi et al., "Synthetic Design of MLCT Excited States. Ligand-Substituted, mono-2,2'-bipyridine Complexes of Ruthenium (II),", *J. Am. Chem. Soc.*, 110(23):7751-7759 (1988).

Chen et al., "Triplet Exciton Confinement in Phosphorescent Polymer Light-Emitting Diodes," *Appl. Phys. Lett*, 82(7):1006-1008 (2003).

Cleave et al., "Harvesting Singlet and Triplet Energy in Polymer LEDs," *Adv. Mat.*, 11(4):285-288 (1999).

Das et al., "Intramolecular Quenching of the Excited State of a tris(2,2'-bipyridyl) Ruthenium (II) Chromophore by Covalently Linked Electron-Accepting Metal Centres," *Polyhedron*, 11(16):2119-2122 (1992).

Demas et al., "Design and Applications of Highly Luminescent Transition Metal Complexes," *Analytical Chemistry*, 63(17):829A-837A (1991).

Gonzalez et al., "A Convenient Synthetic Route to Half-Sandwich Rhodium (III) Complexes of the Tripodal Ligand tris(3,5-dimethylpyrazolyl)methane," *Dalton Transactions*, 1:110-115 (2005).

Gunnoe et al., "Reactions of TpRe(CO)$_2$(THF) with Aromatic Molecules (Tp = Hydridotris (pyrazolyl)borate)," *J. Am. Chem. Soc.*, 120(34):8747-8754 (1998).

Ikai et al., "Highly Efficient Phosphorescence from Organic Light-Emitting Devices with an Exciton-Block Layer," *Appl. Phys. Lett.*, 79(2):156-158 (2001).

Jones et al., "Photochemical Electron Transfer in Chromophore-Quencher Complexes of Ruthenium (II) based on tris(1-pyrazolyl)methane," *Inorganic Chem.*, 32(7):1167-1178 (1993).

Lane et al., "Origin of Electrophosphorescence from a Doped Polymer Light Emitting Diode," *Phys. Rev. B*, 63:235206-1-235206-8 (2001).

Lee et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Lees, "Luminescence Properties of Organometallic Complexes," *Chem. Rev.*, 87:711-743 (1987).

Metcalfe et al., "A Facile Route to Bimetallic Ruthenium Dipyridophenazine Complexes," *Inorganic Chem.*, 43(1):317-323 (2004).

Niu et al., "Thermal Annealing Below the Glass Transition Temperature: A General Way to Increase Performance of Light-Emitting Diodes Based on Copolyfluorenes," *Appl. Phys. Lett.*, 81(4):634-636 (2002).

O'Brien et al., "Electrophosphorescence from a Doped Polymer Light Emitting Diode," *Synth. Met.*, 116:379-383 (2001).

Setayesh et al., "Bridging the Gap Between Polyfluorene and Ladder-Poly-p-phenylene: Synthesis and Characterization of Poly-2,8-indenofluorene," *Macromolecules*, 33(6):2016-2020 (2000).

Xue et al., "Tuning the Excited-State Properties of Luminescent Rhenium (V) Benzylidyne Complexes Containing Phosphorus and Nitrogen Donor Ligands," *Organometallics*, 17(10):1946-1955 (1998).

Yamaguchi et al., "Effects of B and C on the Ordering of $L1_0$-CoPt Thin Films," *Appl. Phys. Lett.*, 79(5):2001-2003 (2001).

Yamamoto, "Electrically Conducting and Thermally Stable π-Conjugated Poly(Arylenes)s Prepared by Organometallic Processes," *Prog. Polym. Sci.*, 17:1153-1205 (1993).

Yang et al., "Efficient Blue Polymer Light-Emitting Diodes from a Series of Soluble Poly(paraphenylene)s," *J. Appl. Phys.*, 79(2):934-939 (1996).

Zhu et al., "Synthesis of New Iridium Complexes and Their Electrophosphorescent Properties in Polymer Light-Emitting Diodes," *J. Mater. Chem.*, 13:50-55 (2003).

Combined Search and Examination Report for Application No. GB0518968.3, dated Feb. 16, 2006.

International Preliminary Report on Patentability for Application No. PCT/GB2006/003438, dated Mar. 18, 2008.

Written Opinion for Application No. PCT/GB2006/003438, dated Jan. 22, 2007.

* cited by examiner

ORGANIC LIGHT-EMITTING DEVICE

BACKGROUND OF THE INVENTION

1. Field of the Invention

The present invention is concerned with an organic light-emitting device containing a metal complex and to a method of making the same. The present invention also is concerned with new metal complexes and to new compositions containing the metal complexes for use in organic light-emitting devices.

2. Related Technology

In the last decade, much effort has been devoted to the improvement of the emission efficiency of light-emitting devices (LEDs) either by developing highly efficient materials or efficient device structures.

Figure 1:
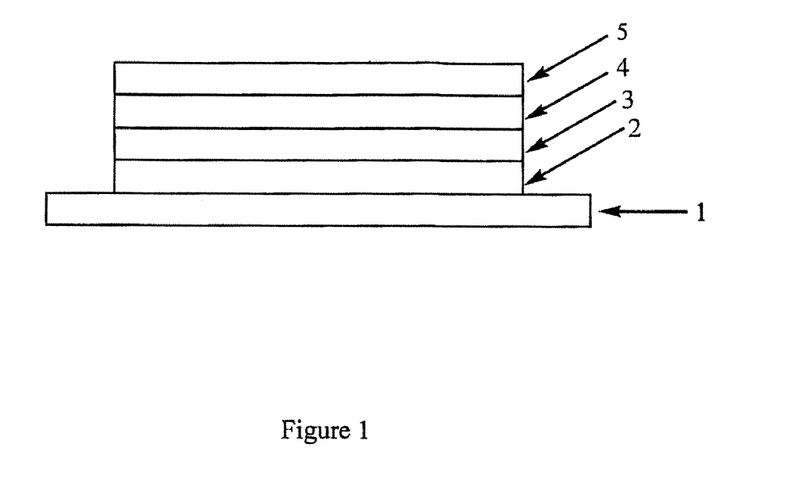
FIG. 1 shows a cross-section of a typical LED.

FIG. 1 shows a cross section of a typical LED. The device has an anode 2, a cathode 5 and a light emissive layer 4 located between the anode and the cathode. The anode may be, for example, a layer of transparent indium-tin oxide. The cathode may be, for example, LiAl. Holes and electrons that are injected into the device recombine radiatively in the light emissive layer. A further feature of the device is the optional hole transport layer 3. The hole transport layer may be a layer of polyethylene dioxythiophene (PEDOT), for example. This provides an energy level which helps the holes injected from the anode to reach the light emissive layer.

Known LED structures also may have an electron transport layer situated between the cathode 5 and the light emissive layer 4. This provides an energy level which helps the electrons injected from the cathode to reach the light emissive layer.

In an LED, the electrons and holes that are injected from the opposite electrodes are combined to form two types of excitons; spin-symmetric triplets and spin-antisymmetric singlets. Radiative decay from the singlets (fluorescence) is fast, but from the triplets (phosphorescence) it is formally forbidden by the requirement of the spin conservation.

In the past few years, many have studied the incorporation by blending of phosphorescent materials into the light emissive layer. Often, the phosphorescent material is a metal complex, however it is not so limited. Further, metal complexes also sometimes are fluorescent.

A metal complex will comprise a metal ion surrounded by ligands. A ligand in a metal complex can have several roles. The ligand can be an "emissive" ligand which accepts electrons from the metal and then emits light. Alternatively, the ligand may be present simply in order to influence the energy levels of the metal to prevent energy loss via non-radiative decay pathways (a "supporting" ligand). For example, it can be advantageous to have strong field ligands as supporting ligands coordinated to the metal to prevent energy loss via non-radiative decay pathways. Common strong field ligands are known to those skilled in this art and include CO, $PPh_3$, and ligands where a negatively charged carbon atom bonds to the metal. N-donor ligands are also strong field ligands, although less so than those previously mentioned.

The effect of supporting ligands can be appreciated from an understanding of the mechanism by which light is emitted from a metal complex. Three reviews of luminescent metal complexes that provide an appreciation of this mechanism are referred to below.

Chem. Rev., 1987, 87,711-7434 is concerned with the luminescence properties of organometallic complexes. This review paper provides a brief summary of the excited states commonly found in organometallic complexes. The excited states that are discussed include metal-to-ligand charge-transfer (MLCT) states, which involve electronic transitions from a metal-centered orbital to a ligand-localized orbital. Thus, in a formal sense this excitation results in metal oxidation and ligand reduction. It is said that the great majority of examples of room temperature emission have been attributed to MLCT excited states.

Analytical Chemistry, Vol. 63, NO, 17, Sep. 1, 1991, 829A to 837A is concerned with the design and applications of highly luminescent transition metal complexes especially those with platinum metals (Ru, Os, Re, Rh and Ir). According to this paper, the most important design rule of luminescent transition metal complexes is that the emission always arises from the lowest excited state. Thus control of the luminescence properties of complexes hinges on control of the relative state energies and the nature and energy of the lowest excited state.

Some luminescent metal complexes having a tridentate ligand coordinated to the metal centre are known.

WO 2004/081017 relates to metal complexes with a hexadentate ligand as active components in the electronics industry.

Dalton Transactions 2005, 1, 110-115 reports the synthesis of [RhCl$_3$tpm*], which it is said is a suitable starting material for the synthesis of heteroleptic half-sandwich complexes.

Inorganic Chemistry 2004, 43 (1), 317-323 discloses the two step synthesis of a bimetallic complex [(tmp)Ru(dppz)$_2$dpp]$^{4+}$.

Organometallics (1998), 17 (10), 1946-1955 is concerned with tuning the excited state properties of luminescent rhenium (V) benzylidyne complexes containing phosphorous and nitrogen donor ligands.

Inorganica Chimica Acta (1994), 226(1-2), 171-7 is concerned with the preparation of a series of binuclear complexes, which are derivatives of [Ru(bpy)$_3$]$^{2+}$.

Inorganic Chemistry 1993, 32(7), 1167-78 is concerned with the preparation and characterisation of Ru-based chromophore-quencher complexes.

Polyhedron (1992), 11 (16), 2119-22 is concerned with intramolecular quenching of the excited state of the tris(2,2'-bipyridyl)ruthenium II chromophore by covalently linked electron-accepting metal centres.

Journal of the American Chemical Society (1988), 110 (23), 7751-9 is concerned with ligand-substituted, mono-2, 2'-bipyridene complexes of ruthenium (II).

J. Am. Chem. Soc. 1998, 120, 8747-8754 is concerned with reactions of TpRe(CO)$_2$(THF) with aromatic molecules. This paper is not concerned with OLEDs and does not mention light emission from the Re complexes.

US 2005/0170207 discloses phosphorescent organic materials used in OLEDs. The materials are metal complexes comprising a multidentate ligand system. A metal is bound to two or more ligands and two or more of the ligands are covalently linked by one or more linking groups.

In view of the above, it will be appreciated that there is a need to identify and design new, stable metal complexes for use in LEDs which provide opportunities for improving efficiency, colour and introducing functionality.

GENERAL DESCRIPTION OF THE INVENTION

Therefore, the present invention provides new metal complexes that can be used to emit light in an LED and LEDs containing the same.

A first aspect of the present invention provides an organic light-emitting device comprising:

an anode;

a cathode;

a light-emitting layer located between the anode and the cathode, said light-emitting layer containing a light-emitting metal complex comprising general formula 1:

(1)

where M represents $Re^{(I)}$, $W^{(O)}$, $Ir^{(III)}$ or $Os^{(II)}$; $L_1$ represents a tridentate ligand; and $L_2$, $L_3$ and $L_4$ represent ligands, characterised in that $L_1$ comprises general formula 2:

(2)

where $R^1$ represents a bridging group; and $Ar^1$, $Ar^2$ and $Ar^3$ each independently represents a group comprising a heteroaryl ring and * indicates coordination to M.

In chemical drawings throughout this specification defining $Ar^1$, $Ar^2$ and/or $Ar^3$ in $L_1$, * indicates coordination to M and —(indicates the bond to $R^1$.

It will be understood that in order for the metal complex to be suitable for use in an OLED, it should be capable of emitting visible light by phosphorescence at room temperature.

Preferably, $L_1$ represents an emissive tridentate ligand. Preferably, $L_2$, $L_3$ and $L_4$ represent supporting ligands.

It will be understood from general formula (2) above that $L_1$ is a facially coordinating tridentate ligand.

In the present metal complex as defined in relation to the first aspect it has been found unexpectedly that ligand $L_1$ helps to minimise quenching of the excited state by non-radiative pathways, specifically vibronic pathways. This can lead to higher photoluminescence efficiency, longer radiative lifetimes and hence higher OLED efficiency. Advantageously, the metal complexes defined in relation to the first aspect may be used as alternatives to metal complexes with Ir cores.

The metal complex may be a MLCT (metal ligand charge transfer) emitter. In the context of the present application, all of the emission from a MLCT emitter or only a component of the emission from a MLCT emitter may be from metal ligand charge transfer. Preferably, at least 5% of the emission from a MLCT emitter is from metal ligand charge transfer.

The metal complex may emit light having a colour anywhere in the range of from blue to green, although this is not essential. By green light is meant radiation having a wavelength in the range of 510-580 nm, preferably 510-570 nm. By blue light is meant radiation having a wavelength in the range of 400-500 nm, more preferably 430-500 nm. Therefore, the metal complex may emit light having a wavelength anywhere in the range of from 400 nm to 580 nm.

The metal complex may emit red light. By red light is meant radiation having a wavelength in the range of 600 to 750 nm, preferably, 600 to 700, more preferably 610 to 650 nm and most preferably having an emission peak around 650 to 660 nm.

Preferably M represents Re(I).

Preferably the metal complex is neutral, although this is not essential. To this end, when M represents a charged metal, $L_1$ preferably is charged. Preferably, the charge on $L_1$ balances the charge on M. When M represents a $Re^{(I)}$, $L_1$ preferably is a monoanionic ligand. When M represents $W^{(o)}$, $L_1$ preferably is a neutral ligand.

If the metal complex is charged, a counterion to balance the charge will be present.

Preferably $L_2$, $L_3$ and $L_4$ are neutral ligands.

$L_2$, $L_3$ and $L_4$ may be the same. However, one of $L_2$, $L_3$ and $L_4$ may be different from the remaining two. This reduces the symmetry of the metal complex.

$L_2$, $L_3$ and $L_4$ may all be different from one another.

Any suitable supported ligands may be used provided that the metal complex emits visible light at room temperature. Suitable supporting ligands may be selected from CO and other less π-acidic ligands, including ligands with substantially no π-acidity, such as THF.

In one embodiment, $L_2=L_3=L_4=CO$.

π-acidity of a monodentate ligand L commonly is measured with reference to the strength of a Ni—CO bond in a L-Ni(CO)$_3$ complex.

The more π-acidic L is, the less back electron donation there is from Ni to CO and the less strong the Ni—CO bond.

The same test can be carried out for bidentate or tridentate ligands by appropriately reducing the number of CO ligands.

Suitable supporting ligands may be selected from less π-acidic ligands such as alkyne, alkene, alkynyl, nitrosyl, cyanide, isocyanide, amine, furan, phosphine and phosphite. For example:

(3)

(4)

Two or all three of $L_2$, $L_3$ and $L_4$ as described herein may be linked so that $L_2$, $L_3$ and $L_4$ together comprise (i) a bidentate ligand and a monodentate ligand or (ii) a tridentate ligand.

A bidentate supporting ligand may comprise formula 5:

(5)

where each $R^2$ independently represents a substituent group such as alkyl, alkoxy, halide (preferably fluoride), or aryl. Phenyl and N-pyrrolyl are preferred substituent groups.

A tridentate supporting ligand may comprise formula 6:

(6)

where $R^2$ is as defined above. $R^2$ may be selected to avoid steric hindrance within the ligand.

Turning to $L_1$, this imparts rigidity to the metal complex and reduces molecular vibrations.

The heteroaryl rings comprised in $Ar^1$, $Ar^2$ and $Ar^3$ offer an advantage because they offer the opportunity to functionalise the ligand. Specific functionalities can be introduced to $Ar^1$, $Ar^2$ and/or $Ar^3$ by way of functional substituents such as solubilising substituents and charge-transporting substituents. Altering the substituents also gives control over the pi acceptor and sigma donor properties of the ligand which in turn influence the various energy levels and hence the colour and efficiency of emission.

$Ar^1$, $Ar^2$ and $Ar^3$ may comprise any suitable heteroaryl groups, for example:

where R represents H or a substituent.

In $Ar^1$, $Ar^2$ and $Ar^3$, the heteroaryl ring preferably coordinates directly to M. However, this is not essential and $Ar^1$, $Ar^2$ and/or $Ar^3$ may coordinate to M via a linking group such as sulphur as shown above or oxygen. $Ar^1$, $Ar^2$ and/or $Ar^3$ may coordinate to M via the nitrogen atom of an amine linking group.

In $Ar^1$, $Ar^2$ and $Ar^3$, the heteroatom in the heteroaryl ring preferably coordinates directly to M.

The heteroaryl rings comprised in $Ar^1$, $Ar^2$ and $Ar^3$ preferably each contain at least one nitrogen heteroatom, more preferably two or three nitrogen heteroatoms.

The heteroaryl rings comprised in $Ar^1$, $Ar^2$ and $Ar^3$ preferably are 5 or 6 membered rings, more preferably 5 or 6 membered rings containing one, two or three nitrogen heteroatoms.

$Ar^1$, $Ar^2$ and $Ar^3$ may be the same or different from one another.

In $Ar^1$, the heteroaryl ring may be conjugatively linked to a second aryl or heteroaryl group. Similarly, in $Ar^2$, the heteroaryl ring may be conjugatively linked to a second aryl or heteroaryl group. Similarly, in $Ar^3$, the heteroaryl ring may be conjugatively linked to a second aryl or heteroaryl group. The second aryl or heteroaryl group may be fused to the heteroaryl ring or linked thereto by a single direct bond.

$Ar^1$, $Ar^2$ and/or $Ar^3$ may comprise a heteroaryl ring having a formula as shown by one of formulae 7 to 15. $Ar^1$, $Ar^2$ and/or $Ar^3$ may comprise a heteroaryl ring having a formula as shown by one of formulae 7 to 15:

(7)

(8)

(9)

(10)

(11)

(12)

(13)

(14)

(15)

where X, Y and Z independently represent a heteroatom. R in formula 13 represents H or a substituent. The heteroaryl ring may be unsubstituted. By "unsubstituted" is meant unsubstituted other than by $R^1$. Alternatively, the heteroaryl ring may have further substituents, in addition to $R^1$. Each of X, Y and Z independently may represent N, P, S, or O. X, Y and Z may be the same or different. In a single heteroaryl ring, preferably all X, Y and Z are the same and preferably represent N.

Formulae 7 to 9 and 12 to 14 are preferred.

$Ar^1$, $Ar^2$ and/or Ar may comprise a substituted heteroaryl ring, for example as shown by one of formulae 16 to 21:

(16)

(17)

(18)

(19)

(20)

(21)

where X and Y are as defined above; $R^3$, $R^4$ and $R^5$ independently represent any suitable substituent and may be the same or different. Suitable substituents may be selected from aryl groups, such as phenyl, heteroaryl, alkyl (including substituted alkyl, such as fluoroalkyl), alkoxy, cyanide, amide, and halide. A substituent may comprise a dendron.

In formulae 16 to 21, preferably X and Y are the same, more preferably X=Y=N, giving formulae 22 to 26:

(22)

(23)

(24)

(25)

(26)

The heteroaryl ring comprised in $Ar^1$, $Ar^2$ and/or $Ar^3$ may be conjugatively linked to a substituent. For example, the heteroaryl rings shown by formulae 7 to 15 may be conjugatively linked to a substituent. The heteroaryl ring may be conjugatively linked to $R^3$ and/or $R^4$ and/or $R^5$ in formulae 17 to 25. Controlling the extent of conjugation in $L_1$ can tune the emission colour. Increasing the conjugation in $L_1$ has been found to red-shift the colour of emission.

When the heteroaryl ring comprised in $Ar^1$, $Ar^2$ and/or $Ar^3$ is conjugatively linked to a substituent advantageously $L_2$, $L_3$ and $L_4$ may be the same, preferably CO. Alternatively, two of $L_2$, $L_3$ and $L_4$ may be the same, preferably CO. When two of $L_2$, $L_3$ and $L_4$ are CO, the third ligand preferably is a less π-acidic ligand.

When the heteroaryl ring comprised in $Ar^1$, $Ar^2$ and/or $Ar^3$ is not conjugatively linked to a substituent or when $Ar^1$, $Ar^2$ and/or $Ar^3$ consists of an unsubstituted heteroaryl ring, preferably no more than two of $L_2$, $L_3$ and $L_4$ represent CO (or another ligand with similar π-acidity), more preferably no more than one. When the heteroaryl ring comprised in $Ar^1$, $Ar^2$ and/or $Ar^3$ is not conjugatively linked to a substituent or when $Ar^1$, $Ar^2$ and/or $Ar^3$ consists of an unsubstituted heteroaryl ring, preferably two or all of $L_2$, $L_3$ and $L_4$ represent less π-acidic ligands than CO.

In formulae 7 to 15, two substituents (in addition to $R^1$) may be present on the heteroaryl ring. The two substituents may be adjacent substituents. The two substituents may be linked so that the substituted heteroaryl ring contains a second ring conjugatively fused to the heteroaryl ring. The second ring may be heteroaryl or aryl. Preferably, the second ring is a 6-membered ring. For example $R^3$ and $R^4$ in formula 17, 19, 23 or 25 may be linked so that the substituted heteroaryl ring contains a second ring conjugatively fused to the heteroaryl ring, for example as shown in formulae 27 to 30:

(27)

(28)

(29)

(30)

The phenyl ring in any one of formulae 27 to 30 may be substituted with one, two, three or four substituents. The substituents may be the same or different. Suitable substituents may be selected from aryl groups, such as phenyl, heteroaryl, alkyl (including substituted alkyl, such as fluoroalkyl), alkoxy, cyanide, amide, and halide. A substituent may comprise a dendron.

The 5-membered heteroaryl ring in any one of formulae 27 to 30 may have a substituent. Suitable substituents may be selected from aryl groups, such as phenyl, heteroaryl, alkyl (including substituted alkyl, such as fluoroalkyl), alkoxy, cyanide, amide, and halide. A substituent may comprise a dendron.

$L_1$ may comprise general formula 31:

(31)

where X and Y each independently represents a heteroatom; $R^1$ represents a bridging group; $Ar^1$, $Ar^2$ and $Ar^3$ independently represent a group comprising a heteroaryl ring, as defined anywhere herein; and * indicates coordination to M.

In formula 31, each of X and Y independently may represent N, P, S, or O. Preferably in $L_1$ all X are the same and all Y are the same although this is not essential. Preferably all X and Y are the same and preferably represent N:

(32)

When $Ar^1$, $Ar^2$ and $Ar^3$ are the same, for convenience, formula 31 may be drawn as formula 33:

(33)

where Ar represents a heteroaryl ring as described anywhere herein.

Referring to the bridging group $R^1$, $R^1$ typically will represent where $R^5$ is H or a substituent group. Suitable substituent groups include alkyl, aryl, and heteroaryl groups, and organic dendrons to improve solubility or processability. When $R^1$ represents this confers a negative charge on $R^1$, which may be useful for balancing the charge on M, for example when M is $Re^{(I)}$.

Other suitable $R^1$ groups include:

where $R^6$ is H or a substituent group. $R^6$ may represent an anionic group, for example $SO_3^-$, $BF_3^-$, $O^-$, or $CO_2^-$, in order to confer a negative charge on $R^1$.

$R^1$ may be selected to tune the wavelength of emission, for example by further increasing conjugation. Therefore, $R^1$ may be conjugatively linked to $Ar^1$, $Ar^2$ and/or $Ar^3$.

The metal complex may comprise formula 34:

(34)

where M and $R^1$ are as defined anywhere herein and $L_2$ represents a less π-acidic ligand than CO. Preferably M represents Re, for example as shown in formula 35 or formula 36:

(35)

where R represents a substituent group such as alkyl, aryl, halide, alkoxy, amide, or an anionic N-coordinated nitrogen heterocycle. The nitrogen heterocycle may be conjugated, for example pyrollyl, or may be non-conjugated.

(36)

where R represents an alkyl group such as t-Bu.

The metal complex may comprise formula 37:

(37)

where M and $R^1$ are as defined anywhere herein and $L_2$ represents a less π-acidic ligand than CO. Preferably M represents Re, for example as shown in formula 38 or formula 39:

(38)

where R represents a substituent group such as alkyl, aryl, halide, alkoxy, amide, or an anionic N-coordinated nitrogen heterocycle. The nitrogen heterocycle may be conjugated, for example pyrollyl, or may be non-conjugated.

(39)

where R represents an alkyl group such as t-Bu.

The phenyl ring in any one of formulae 34 to 39 may be substituted with one, two, three or four substituents. The substituents may be the same or different. Suitable substituents may be selected from aryl groups, such as phenyl, heteroaryl, alkyl (including substituted alkyl, such as fluoroalkyl), alkoxy, cyanide, amide, and halide. A substituent may comprise a dendron.

The metal complex may comprise formula 67:

(67)

where M and R$^1$ are as defined anywhere herein and at least one of L$_2$ and L$_3$ represents a less π-acidic ligand than CO. Preferably, L$_2$ and L$_3$ represent less π-acidic ligands than CO. Preferably M represents Re, for example as shown in formula 40:

(40)

The metal complex may comprise formula 41:

(41)

where M and R$^1$ are as defined anywhere herein and L$_2$ and L$_3$ independently represent CO or a less π-acidic ligand than CO. Preferably, at least one of L$_2$ and L$_3$ represents a less π-acidic ligand than CO. More preferably, L$_2$ and L$_3$ represent less π-acidic ligands than CO. Preferably M represents Re, for example as shown in formula 42:

(42)

The metal complex may comprise formula 43:

(43)

where M and R$^1$ are as defined anywhere herein and L$_2$ and L$_3$ independently represent CO or a less π-acidic ligand than CO. Preferably, at least one of L$_2$ and L$_3$ represents a less π-acidic ligand than CO. Preferably, L$_2$ and L$_3$ represent less π-acidic ligands than CO. Preferably M represents Re, for example as shown in formula 44:

(44)

R$^1$ in formulae 34, 37, 67, 41 and/or 43 may be selected to tune the wavelength of emission, for example by further increasing conjugation.

In formula 34 to 44 and 67, the heteroaryl ring shown may be further substituted.

A second aspect of the present invention provides novel metal complexes as defined in relation to the first aspect. In particular, the second aspect provides a light-emitting metal complex comprising general formula 1:

(1)

Where M represents Re$^{(I)}$, W$^{(0)}$, Ir$^{III}$, or Os$^{II}$; L$_1$ represents a tridentate ligand; and L$_2$, L$_3$ and L$_4$ independently represent ligands, characterised in that L$_1$ comprises general formula 2:

(2)

where R$^1$ represents a bridging group; and Ar$^1$, Ar$^2$ and Ar$^3$ independently represent a group comprising a heteroaryl ring; and * indicates coordination to M, characterised in that the heteroaryl rings comprised in Ar$^1$, Ar$^2$ and Ar$^3$ are each independently conjugatively linked to an aryl or heteroaryl group.

In Ar$^1$, the heteroaryl ring may be conjugatively fused to the respective aryl or heteroaryl group or may be conjugatively linked thereto by a single direct bond. Similarly, in Ar$^2$, the heteroaryl ring may be conjugatively fused to the respective aryl or heteroaryl group or may be conjugatively linked thereto by a single direct bond. Similarly, in Ar$^3$, the heteroaryl ring may be conjugatively fused to the respective aryl or heteroaryl group or may be conjugatively linked thereto by a single direct bond.

Light-emitting metal complexes according to the second aspect of the present invention have been found to be advantageous because, for Re$^{(I)}$ and W$^{(O)}$ complexes, the conjugation in the tridentate ligand L$_1$ allows the emission colour of the metal complex to be tuned.

The metal complex according to the second aspect may be as defined anywhere above in relation to the metal complex in the first aspect, provided that the respective heteroaryl rings comprised in $Ar^1$, $Ar^2$ and $Ar^3$ are each independently conjugatively linked to an aryl or heteroaryl group.

In particular, preferred M, and supporting ligands $L_2$, $L_3$ and $L_4$ are as described in relation to the first aspect.

With regard to $L_1$, when M represents $Re^I$, $L_1$ preferably is a monoanionic ligand. When M represents $W^{(O)}$, $L_1$ preferably is a neutral ligand.

Preferred $L_1$ are as described in relation to the first aspect provided that the heteroaryl rings comprised in $Ar^1$, $Ar^2$ and $Ar^3$ are each independently conjugatively linked to an aryl or heteroaryl group.

Suitable heteroaryl rings to be comprised in $Ar^1$, $Ar^2$ and $Ar^3$ include those shown in formulae 7 to 26 as defined in relation to the first aspect.

The aryl or heteroaryl substituent on the heteroaryl ring in $Ar^1$, $Ar^2$ and/or $Ar^3$ preferably comprises a 6-membered ring, such as phenyl.

The aryl or heteroaryl substituent may be situated at any suitable position on the heteroaryl ring. There may be one or more than one, for example two, aryl or heteroaryl groups on the heteroaryl ring.

The aryl or heteroaryl substituent may be fused to the heteroaryl ring, for example as shown in any one of formulae 27 to 30 as defined in relation to the first aspect.

$L_1$ may comprise general formula 31, 32 or 33 as defined in relation to the first aspect.

Referring to the bridging group $R^1$, $R^1$ may be as described anywhere above in relation to the first aspect.

The $L_1$ ligand in the metal complex according to the second aspect may or may not be symmetric.

A third aspect of the present invention provides a method for making a device as defined in relation to the first aspect. The light-emissive layer containing the metal complex may be formed by solution processing, for example by spin-coating.

A fourth aspect of the present invention provides a method for making a metal complex as defined in relation to the second aspect. The desired ligands may be introduced into the metal complex by suitable ligand exchange reactions. Such reactions will be known to those skilled in the art. The tridentate ligand $L_1$ may be introduced into the metal complex by a ligand exchange reaction, for example by the replacement of three monodentate ligands in a metal complex. When $L_1$ is charged, the ligands it replaces must collectively have the same charge as $L_1$. For example, in the case of a $Re^{(I)}$ complex, $L^1$ preferably has a charge of $-1$. Therefore, the ligands it replaces must collectively have a charge of $-1$, for example two neutral unidentate ligands (e.g. CO) and one monoanionic unidentate ligand (e.g. CI).

BRIEF DESCRIPTION OF THE DRAWINGS

The present invention will now be described in more detail with reference to the attached figures, in which.

DETAILED DESCRIPTION

Figure 2:
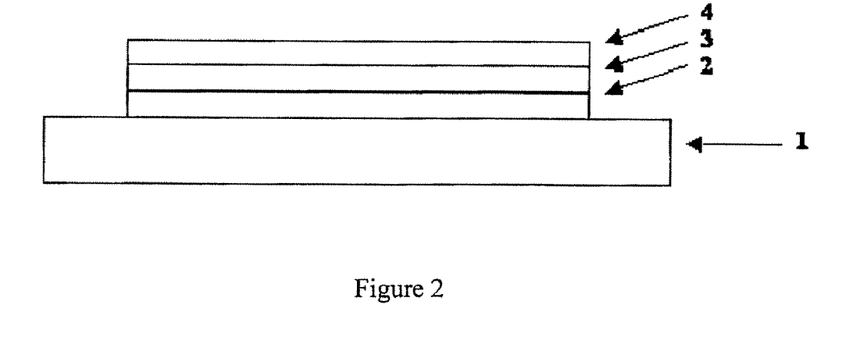
FIG. 2 shows the architecture of an OLED according to the invention comprising a transparent glass or plastic substrate 1, an anode 2 of indium tin oxide and a cathode 4. A light-emitting layer 3 is provided between anode 2 and cathode 4.
Figure 3:
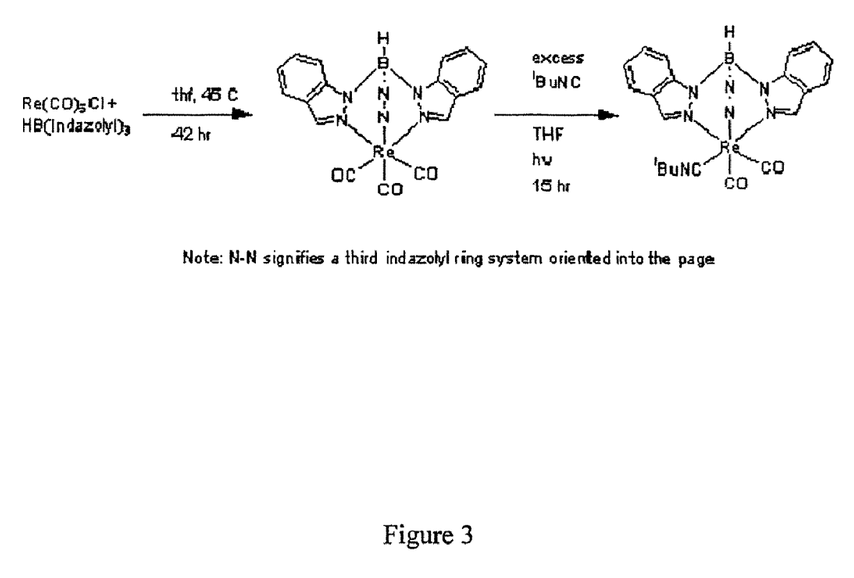
FIG. 3 shows the reaction scheme for the preparation of metal complexes 1 and 2 in Examples 1 and 2.

Further layers may be located between anode 2 and cathode 3, such as charge transporting, charge injecting or charge blocking layers.

In particular, it is desirable to provide a conductive hole injection layer formed of a doped organic material located between the anode 2 and the electroluminescent layer 3 to assist hole injection from the anode into the layer or layers of semiconducting polymer. Examples of doped organic hole injection materials include poly(ethylene dioxythiophene) (PEDT), in particular PEDT doped with polystyrene sulfonate (PSS) as disclosed in EP 0901176 and EP 0947123, or polyaniline as disclosed in U.S. Pat. Nos. 5,723,873 and 5,798,170.

If present, a hole transporting layer located between anode 2 (or a hole injection layer when present) and light-emitting layer 3 preferably has a HOMO level of less than or equal to 5.5 eV, more preferably around 4.8 to 5.5 eV.

If present, an electron transporting layer located between light-emitting layer 3 and cathode 4 preferably has a LUMO level of around 3 to 3.5 eV.

The light-emitting layer 3 comprises the metal complex and a host material. Preferably, the host material has a $T_1$ higher than that of the emitter, although it may be the same or even slightly lower in some cases. The host material may be mixed with the metal complex or the metal complex may be covalently bound to the host material. The light-emitting layer may comprise one or more further materials. In particular, the metal complex and host material may be blended with hole and/or electron transporting materials as disclosed in, for example, WO 99/48160. The metal complex may be covalently bound to a charge transporting material.

Numerous hosts for metal complexes are described in the prior art including "small molecule" hosts such as 4,4'-bis(carbazol-9-yl)biphenyl), known as CBP, and (4,4',4"-tris(carbazol-9-yl)triphenylamine), known as TCTA, disclosed in Ikai et al. (Appl. Phys. Lett., 79 no. 2, 2001, 156); and triarylamines such as tris-4-(N-3-methylphenyl-N-phenyl)phenylamine, known as MTDATA. Polymers are also known as hosts, in particular homopolymers such as poly(vinyl carbazole) disclosed in, for example, Appl. Phys. Lett. 2000, 77(15), 2280; polyfluorenes in Synth. Met. 2001, 116, 379, Phys. Rev. B 2001, 63, 235206 and Appl. Phys. Lett. 2003, 82(7), 1006; poly[4-(N-4-vinyl benzyloxyethyl, N-methylamino)-N-(2,5-di-tertbutylphenyl-napthalimide] in Adv. Mater. 1999, 11(4), 285; and poly(para-phenylenes) in J. Mater. Chem. 2003,13,50-55. Copolymers also are known as hosts.

Cathode 4 is selected from materials that have a workfunction allowing injection of electrons into the electroluminescent layer. Other factors influence the selection of the cathode such as the possibility of adverse interactions between the cathode and the electroluminescent material. The cathode may consist of a single material such as a layer of aluminium. Alternatively, it may comprise a plurality of metals, for example a bilayer of calcium and aluminium as disclosed in WO 98/10621, elemental barium disclosed in WO 98/57381, Appl. Phys. Lett. 2002, 81(4), 634 and WO 02/84759 or a thin layer of dielectric material to assist electron injection, for example lithium fluoride disclosed in WO 00/48258 or barium fluoride, disclosed in Appl. Phys. Lett. 2001, 79(5), 2001. In order to provide efficient injection of electrons into the device, the cathode preferably has a workfunction of less than 3.5 eV, more preferably less than 3.2 eV, and most preferably less than 3 eV.

Optical devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device is preferably encapsulated with an encapsulant (not shown) to prevent ingress of moisture and oxygen. Suitable encapsulants include a sheet of glass, films having suitable barrier properties such as alternating stacks of polymer and dielectric as disclosed in, for example, WO 01/81649 or an airtight container as disclosed in, for example, WO 01/19142. A getter material for absorption of any atmospheric moisture and/or oxygen that may permeate through the substrate or encapsulant may be disposed between the substrate and the encapsulant.

In a practical OLED, at least one of the electrodes is semi-transparent in order that light may be absorbed (in the case of a photoresponsive device) or emitted (in the case of an OLED). Where the anode is transparent, it typically comprises indium tin oxide. Examples of transparent cathodes are disclosed in, for example, GB 2348316.

The embodiment of FIG. 2 illustrates a device wherein the device is formed by firstly forming an anode on a substrate followed by deposition of an electroluminescent layer and a cathode, however it will be appreciated that the device of the invention could also be formed by firstly forming a cathode on a substrate followed by deposition of an electroluminescent layer and an anode.

Charge transporting polymers preferably comprise a first repeat unit selected from arylene repeat units, in particular: 1,4-phenylene repeat units as disclosed in J. Appl. Phys. 1996, 79, 934; fluorene repeat units as disclosed in EP 0842208; indenofluorene repeat units as disclosed in, for example, Macromolecules 2000, 33(6), 2016-2020; and spirofluorene repeat units as disclosed in, for example EP 0707020. Each of these repeat units is optionally substituted. Examples of substituents include solubilising groups such as $C_{1-20}$ alkyl or alkoxy; electron withdrawing groups such as fluorine, nitro or cyano; and substituents for increasing glass transition temperature (Tg) of the polymer.

Particularly preferred charge transport polymers comprise optionally substituted, 2,7-linked fluorenes, most preferably repeat units of formula 45:

(45)

wherein $R^5$ and $R^6$ are independently selected from hydrogen or optionally substituted alkyl, alkoxy, aryl, arylalkyl, heteroaryl and heteroarylalkyl. More preferably, at least one of $R^5$ and $R^6$ comprises an optionally substituted $C_4$-$C_{20}$ alkyl or aryl group.

A polymer comprising the first repeat unit may provide one or more of the functions of hole transport, electron transport and emission depending on which layer of the device it is used in and the nature of co-repeat units.

In particular:
a homopolymer of the first repeat unit, such as a homopolymer of 9,9-dialkylfluoren-2,7-diyl, may be utilised to provide electron transport.

a copolymer comprising a first repeat unit and a triarylamine repeat unit, in particular a repeat unit selected from formulae 46-51, may be utilised to provide hole transport:

46

47

48

49

50

51 wherein $A^1$, $B^1$, A, B, C and D are independently selected from H or a substituent. More preferably, one or more of $A^1$, $B^1$, A, B, C and D is independently selected from the group consisting of optionally substituted, branched or linear alkyl, aryl, perfluoroalkyl, thioalkyl, cyano, alkoxy, heteroaryl, alkylaryl and arylalkyl groups. Most preferably, $A^1$, $B^1$, A and B are $C_{1-10}$ alkyl.

Particularly preferred hole transporting polymers of this type are AB copolymers of the first repeat unit and a triarylamine repeat unit.

a copolymer comprising a first repeat unit and heteroarylene repeat unit may be utilised for charge transport. Preferred heteroarylene repeat units are selected from formulae 52 to 66:

(52)

wherein $R^7$ and $R^8$ are the same or different and are each independently hydrogen or a substituent, preferably alkyl, aryl, perfluoroalkyl, thioalkyl, cyano, alkoxy, heteroaryl, alkylaryl or arylalkyl. For ease of manufacture, $R^7$ and $R^8$ are preferably the same. More preferably, they are the same and are each a phenyl group.

(53)

(54)

(55)

(56)

-continued (57)

(58)

(59)

(60)

(61)

(62)

(63)

(64)

Preferred methods for preparation of these conjugated polymers are Suzuki polymerisation as described in, for example, WO 00/53656 and Yamamoto polymerisation as described in, for example, T. Yamamoto, "Electrically Conducting And Thermally Stable p-Conjugated Poly(arylene)s Prepared by Organometallic Processes", Progress in Polymer Science 1993, 17, 1153-1205. These polymerisation techniques both operate via a "metal insertion" wherein the metal atom of a metal complex catalyst is inserted between an aryl group and a leaving group of a monomer. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units and end groups comprising aryl groups as illustrated throughout this application may be derived from a monomer carrying a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halides, other leaving groups capable of participating in metal insertion include groups include tosylate, mesylate and triflate.

To form the OLED, charge transporting polymers may be deposited from solution to form a layer. Suitable solvents for polyarylenes, in particular polyfluorenes, include mono- or poly-alkylbenzenes such as toluene and xylene. Particularly preferred solution deposition techniques are spin-coating and inkjet printing.

Spin-coating is particularly suitable for devices wherein patterning of the electroluminescent material is unnecessary—for example for lighting applications or simple monochrome segmented displays.

Inkjet printing is particularly suitable for high information content displays, in particular full colour displays. Inkjet printing of OLEDs is described in, for example, EP 0880303.

If multiple layers of the device are formed by solution processing then the skilled person will be aware of techniques to prevent intermixing of adjacent layers, for example by crosslinking of one layer before deposition of a subsequent layer or selection of materials for adjacent layers such that the material from which the first of these layers is formed is not soluble in the solvent used to deposit the second layer.

EXAMPLES

Example 1

Preparation of [HB(Indazolyl)$_3$]Re(Co)$_3$ (metal complex 1)

The reaction was performed under an atmosphere of dry dinitrogen gas.

To a 1:1 w/w mixture of Re(CO)$_5$Cl (commercially available) and K[HB(Indazolyl)$_3$] (commercially available) was added dry THF. The reaction mixture was stirred, and heated to 50 degrees C. for 42 hr, during which time a solid precipitated. The reaction mixture was filtered, and the volatiles removed to give the crude product. Recrystallisation of the solid from THF/hexane afforded colourless crystals of [HB(Indazolyl)$_3$]Re(CO)$_3$.

[HB(Indazolyl)$_3$] represents a hydrotris(indazolyl)borato ligand.

Example 2

Preparation of [HB(Indazolyl)$_3$]Re(CO)$_2$(CN$^t$Bu) (metal complex 2)

The reaction was performed using quartz glassware.

A solution of [HB(Indazolyl)$_3$]Re(CO)$_3$ from Example 1 and excess CN$^t$Bu (commercially available) in THF was irradiated for 15 hours using a mercury arc lamp. After 15 hours the irradiation was halted, the solution concentrated under vacuum and the product precipitated by the addition of methanol. The product was isolated by filtration and purified by recrystallisation from THF/hexane.

Example 3

Preparation of device (A) containing metal complex 1 and device (B) containing metal complex 2

(A) Poly(ethylene dioxythiophene)/poly(styrene sulfonate) (PEDT/PSS), available from H C Starck of Leverkusen, Germany as Baytron P® was deposited over an indium tin oxide anode supported on a glass substrate (available from Applied Films, Colorado, USA) by spin coating. A hole transporting layer of F8-TFB (shown below) was deposited over the PEDT/PSS layer by spin coating from xylene solution to a thickness of about 10 nm and heated at 180° C. for 1 hour. Metal complex 1 from Example 1 was deposited over the layer of F8-TFB by spin-coating from xylene solution in a PVK host to a thickness of around 65 nm. The ratio of metal complex to host was 5 wt %:95 wt %. A Ba/Al cathode was formed over the metal complex layer by evaporating a first layer of barium to a thickness of up to about 10 nm and a second layer of aluminium barium to a thickness of about 100 nm over the semiconducting polymer. Finally, the device was sealed using a metal enclosure containing a getter that is placed over the device and glued onto the substrate in order to form an airtight seal.

"F8-TFB"

(B) The above method was repeated using metal complex 2 in place of metal complex 1 to make a second device according to the invention.

The invention claimed is:
1. An organic light-emitting device comprising:
an anode;
a cathode;
a light-emitting layer located between the anode and the cathode, said light-emitting layer containing a light-emitting metal complex comprising general formula 1:

(1)

where M represents $Re^{(I)}$; $L_1$ represents a tridentate ligand; and $L_2$, $L_3$ and $L_4$ represent ligands, wherein $L_1$ comprises general formula 2:

(2)

where $R^1$ represents a bridging group; and $Ar^1$, $Ar^2$ and $Ar^3$ each independently represents a group comprising a heteroaryl ring and * indicates coordination to M.

2. An organic light-emitting device comprising:
an anode;
a cathode;
a light-emitting layer located between the anode and the cathode, said light-emitting layer containing a light-emitting metal complex comprising general formula 1:

(1)

where M represents $Re^{(I)}$, $W^{(0)}$, $Ir^{(III)}$, or $Os^{(II)}$; $L_1$ represents a tridentate ligand; and $L_2$, $L_3$ and $L_4$ represent ligands, wherein $L_1$ comprises general formula 2:

(2)

where $R^1$ represents a bridging group; and $Ar^1$, $Ar^2$ and $Ar^3$ each independently represents a group comprising a heteroaryl ring and * indicates coordination to M, where $Ar^1$, $Ar^2$ and/or $Ar^3$ comprises a heteroaryl ring having a formula as shown by one of formulae 7 to 11:

(7)

(8)

(9)

(10)

(11)

where * indicates coordination to M; X, Y and Z each independently represent a heteroatom; and ┤ indicates the bond to $R^1$, and wherein two substituents in addition to $R^1$ are present on the heteroaryl ring in each of formulae 7 to 11, the two substituents being linked so that the heteroaryl ring has a second ring conjugatively fused thereto.

3. A device according to claim 2, wherein $Ar^1$, $Ar^2$ and/or $Ar^3$ comprises a group having formula 27 or 28:

(27)

-continued (28)

where * indicates coordination to M; X represents a heteroatom; and ―(―indicates the bond to $R^1$.

4. An organic light-emitting device comprising:
an anode;
a cathode;
a light-emitting layer located between the anode and the cathode, said light-emitting layer containing a light-emitting metal complex comprising general formula 1:

(1)

where M represents $Re^{(I)}$, $W^{(0)}$, $Ir^{(III)}$, or $Os^{(II)}$; $L_1$ represents a tridentate ligand; and $L_2$, $L_3$ and $L_4$ represent ligands, wherein $L_1$ comprises general formula 2:

(2)

where $R^1$ represents a bridging group; and $Ar^1$, $Ar^2$ and $Ar^3$ each independently represents a group comprising a heteroaryl ring and * indicates coordination to M, wherein the metal complex comprises formula 34, 37, 67, 41 or 43:

(34)

where M and $R^1$ are as defined in any preceding claim and $L_2$ represents a less π-acidic ligand than CO:

(37)

Where M and $R^1$ are as defined in any preceding claim and $L_2$ represents a less π-acidic ligand than CO:

(67)

Where M and $R^1$ are as defined in any preceding claim and at least one of $L_2$ and $L_3$ represents a less π-acidic ligand than CO:

(41)

Where M and $R^1$ are as defined in any preceding claim and $L_2$ and $L_3$ independently represent CO or a less π-acidic ligand than CO:

(43)

Where M and $R^1$ are as defined in any preceding claim and $L_2$ and $L_3$ independently represent CO or a less π-acidic ligand than CO.

* * * * *